United States Patent [19]
Korteweg et al.

[11] Patent Number: 5,584,827
[45] Date of Patent: Dec. 17, 1996

[54] NASAL-PACKING ARTICLE

[75] Inventors: George P. Korteweg, Mystic; Wayne Korteweg, Ledyard, both of Conn.

[73] Assignee: Ultracell Medical Technologies, Inc, North Stonington, Conn.

[21] Appl. No.: 295,109

[22] Filed: Aug. 24, 1994

Related U.S. Application Data

[63] Continuation-in-part of Ser. No. 149,217, Nov. 5, 1993, abandoned, which is a continuation-in-part of Ser. No. 884,204, May 18, 1992, abandoned.

[51] Int. Cl.⁶ .............................. A61F 13/15; A61F 13/20
[52] U.S. Cl. .......................... 604/369; 604/358; 604/904; 604/285; 604/374; 604/379; 604/11; 604/385.1; 606/196
[58] Field of Search .................... 606/191, 196, 606/199; 604/285–288, 369, 374, 377, 378, 385.1, 379–380, 1–3, 11–18, 904, 358; 602/46–47, 57

[56] References Cited

U.S. PATENT DOCUMENTS

| | | |
|---|---|---|
| D. 287,880 | 1/1987 | Doyle . |
| 1,537,992 | 5/1925 | Gearon . |
| 1,732,697 | 10/1929 | Ryan . |
| 1,964,911 | 7/1934 | Haas ............................... 604/377 |
| 2,057,206 | 10/1936 | Pohl ............................... 604/377 |
| 2,110,962 | 3/1938 | Munro ............................. 128/271 |
| 2,179,964 | 11/1939 | Stevens ........................... 128/148 |
| 2,499,414 | 3/1950 | Rabell ............................ 128/285 |
| 2,739,593 | 3/1956 | McLaughlin ...................... 128/263 |
| 2,917,049 | 12/1959 | Delaney .......................... 604/904 |
| 3,049,125 | 8/1962 | Kriwkowitsch .................... 128/325 |
| 3,079,921 | 3/1963 | Brecht et al. .................... 604/380 |
| 3,084,689 | 4/1963 | Maro ............................. 128/270 |
| 3,306,294 | 2/1967 | Penksa ........................... 128/285 |
| 3,369,544 | 2/1968 | Crockford ........................ 128/285 |
| 3,397,695 | 8/1968 | Voss ............................. 604/904 |
| 3,570,494 | 3/1971 | Gottschalk ....................... 128/325 |
| 3,762,414 | 10/1973 | Burnhill ......................... 128/285 |
| 3,791,385 | 2/1974 | Davis et al. ..................... 128/263 |
| 3,965,905 | 6/1976 | Schoenholz et al. ................ 604/904 |
| 4,030,504 | 6/1977 | Doyle ............................ 128/325 |
| 4,159,719 | 7/1979 | Haerr ............................ 604/286 |
| 4,175,561 | 11/1979 | Hirschman ....................... 128/296 |
| 4,568,326 | 2/1986 | Rangaswamy ....................... 604/1 |
| 4,646,739 | 3/1987 | Doyle ............................ 128/325 |
| 4,950,280 | 8/1990 | Brennan .......................... 606/196 |
| 5,047,024 | 9/1991 | Glassman ......................... 604/380 |
| 5,350,371 | 9/1994 | Van Iten ......................... 604/378 |
| 5,383,891 | 1/1995 | Walker ........................... 606/196 |
| 5,387,206 | 2/1995 | Valentine et al. ................. 604/385.1 |

FOREIGN PATENT DOCUMENTS

| | | |
|---|---|---|
| 550047 | 12/1957 | Canada . |
| 718042 | 1/1932 | France . |
| 220978 | 6/1968 | Sweden . |

Primary Examiner—John G. Weiss
Assistant Examiner—Bruce E. Snow
Attorney, Agent, or Firm—Ira S. Dorman

[57] ABSTRACT

A nasal packing article, made from a material that is expansible when wetted, is formed with a plurality of laminae that are independently movable and separable from one another, and that expand to effectively exert hemostatic pressure. The article may comprise an assembly of layers interengaged in face-to-face contact, or it may be defined by slits that extend entirely through the thickness or width of the body but terminate short of one end, to leave the laminae connected thereat.

22 Claims, 3 Drawing Sheets

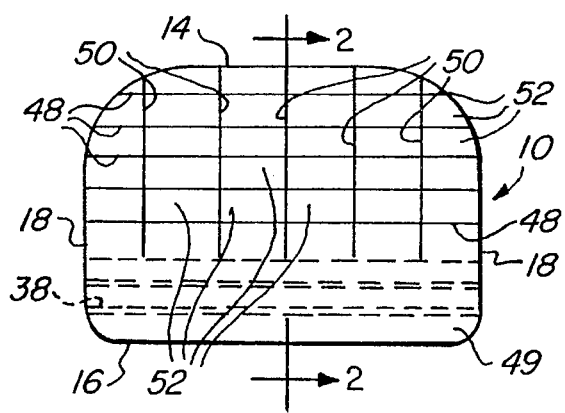
FIG. 1
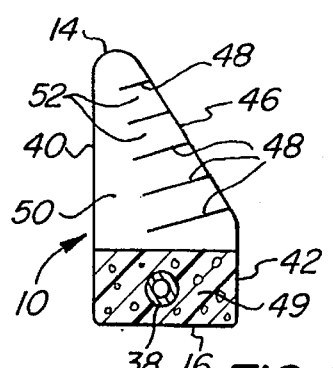
FIG. 2A
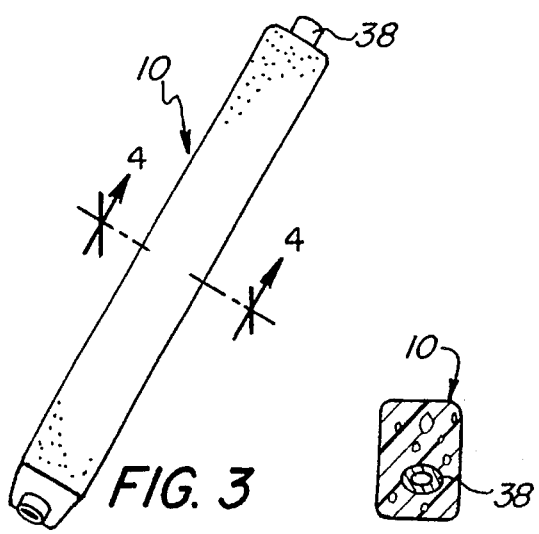
FIG. 3
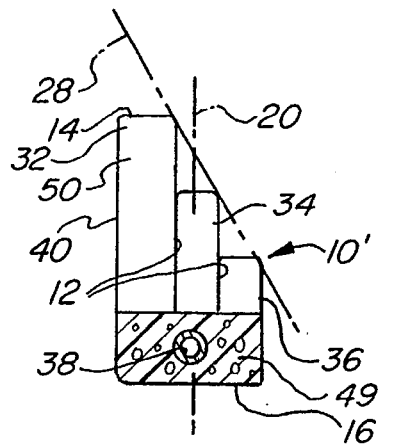
FIG. 2B
FIG. 4
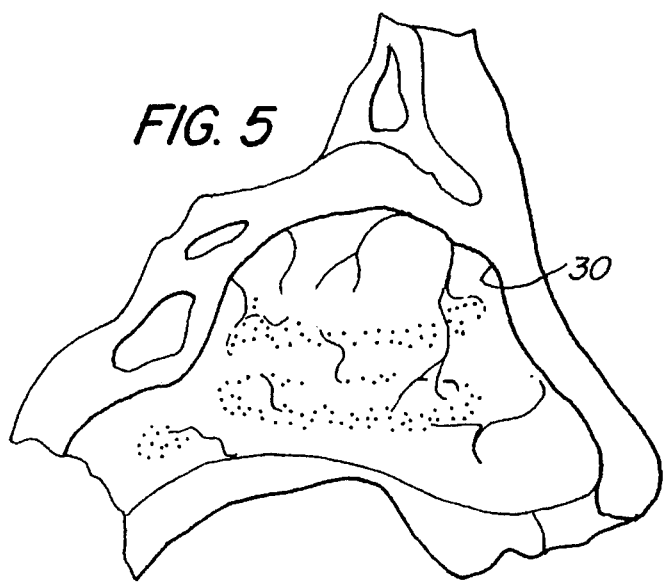
FIG. 5
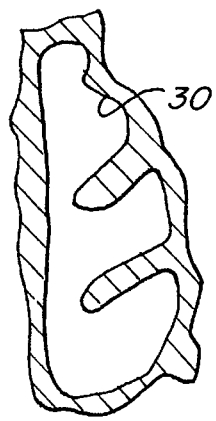
FIG. 6

NASAL-PACKING ARTICLE

CROSS REFERENCE TO RELATED APPLICATION

This application is a continuation-in-part of application Ser. No. 08/149,217, filed Nov. 5, 1993, which in turn is a continuation-in-part of application Ser. No. 07/884,204, filed May 18, 1992, both now abandoned.

BACKGROUND OF THE INVENTION

This invention relates to nasal packing made from sponge-like materials that are expansible from a dry state to form soft, resilient, absorbent bodies.

In U.S. Pat. No. 1,732,697, Ryan discloses a medicated, compressed sponge that is adapted for insertion into the nose, and that swells into contact with the irregular surface portions of the nasal cavity, when moistened. Similarly, Stevens U.S. Pat. No. 2,179,964, Kriwkowitsch U.S. Pat. No. 3,049,125, Gottschalk U.S. Pat. No. 3,570,494, Doyle U.S. Pat. Nos. 4,030,504, 4,646,739, and Des. 287,880, Rangaswamy U.S. Pat. No. 4,568,326, Brennan U.S. Pat. No. 4,950,280, and Sweden Patent No. 220,978 provide nasal hemostats and the like. Medical, catamenial, and like devices are disclosed in the following United States patents: Gearon U.S. Pat. No. 1,537,992, Munro U.S. Pat. No. 2,110,962, Robell U.S. Pat. No. 2,499,414, McLaughlin U.S. Pat. No. 2,739,593, Maro et al U.S. Pat. No. 3,084,689, Penska U.S. Pat. No. 3,306,294, Crockford U.S. Pat. No. 3,369,544, Burnhill U.S. Pat. No. 3,762,414, Davis et al U.S. Pat. No. 3,791,385, and Hirschman U.S. Pat. No. 4,175,561, and in Canada Patent No. 550,047 and France Patent No. 718,042.

Efficient hemostasis, such as after septal, sinus, or rhinoplastic surgery, or to abate nasal hemorrhage, requires the application of gentle pressure to ruptured major arteries and blood vessels over substantially all parts of the nasal cavity. It is not believed that the hemostatic devices provided heretofore function entirely adequately in those respects.

SUMMARY OF THE INVENTION

Accordingly, it is the broad object of the present invention to provide a novel nasal-packing article that is expansible from the dry state.

A more specific object is to provide such an article that is effective to apply gentle pressure to substantially all parts of the nasal cavity, including relatively inaccessible openings and recesses thereof.

Related objects are to provide such an article which avoids undue pressure in or overpacking of the nasal cavity, which is readily inserted and removed and is comfortably worn, which is of simple and inexpensive manufacture, and which functions without need for any supplemental packing, such as with gauze, cotton, or the like.

It has now been found that certain of the foregoing and related objects of the invention are attained by the provision of a novel laminar nasal-packing article fabricated from a porous, absorbent material that is compressible when dry to a dimensionally stable form, and is expansible from its dry, compressed state when wetted and is resiliently deformable in its wet, expanded state. The article comprises a plurality of laminae; each lamina has opposite ends, opposed transverse faces and opposed lateral faces, and has a length dimension taken between the opposite ends, and thickness and width dimensions taken, respectively, between the opposed transverse faces and the opposed lateral faces. The laminae are disposed in face-to-face contact, and are compressed together in at least one of two directions, i.e., perpendicular to the contacting faces and/or parallel thereto. As a result, the laminae are united in a stable, dry, compressed state of mutual bonding over the areas of contact, and they are disengageable, inwardly from one end and along at least a major portion of the length of the article, to enable at least partial delamination and removal.

Generally, each of the laminae will be of uniform thickness, and they may indeed be substantially identical. Alternatively, laminae of different shapes and thicknesses will in some instances be employed to advantage; for example, at least one of the laminae may be substantially thinner than at least one other laminae. Although all faces of the several laminae will usually be substantially planar, laminae having nonplanar faces (e.g., corrugated, zigzag, etc.) may also be employed.

In certain embodiments, at least one of the laminae will advantageously be fabricated from a material that is substantially different from the material used for at least one other laminae. Two exterior laminae may for example be fabricated from a material having pores that are of substantially smaller average size than the pores of the material used for interior laminae. In most instances the article will comprise at least five laminae, and will have an overall thickness, in its fully expanded and unattenuated form, of at least about 10 mm. One or more of the laminae may be subdivided, along at least one plane extending lengthwise of the article and perpendicular to its contacting faces, into a plurality of substantially independent fingers. The article will most desirably be uncompressed in the direction of its length (albeit shorter in the dry state due to shrinkage), and it may further include a hollow tubular element, oriented lengthwise and extending entirely through the packing.

In certain preferred embodiments the article will additionally include connecting means, adjacent one end, for more permanently securing the laminae together. Such connecting means may for example take the form of an adhesive bond, a fusion bond, a substantially rigid mechanical fastener, or a string, the latter being advantageous not only to indicate the presence of packing in the nostril but also to facilitate withdrawal. Alternatively, the article may be constituted of a single piece of the material, partially severed to form the laminae and with an unsevered end section providing the connecting means.

In one specific form the body of the article may have an upper portion that is of upwardly diminishing cross sectional dimensions, taken in planes extending lengthwise and perpendicular to its lateral surface portions, with a lateral surface portion that converges generally toward an intermedial plane to which the other lateral surface portion extends substantially parallel. The body of such an article may desirably have a bottom margin that is substantially rectilinear, and a top margin that merges with the bottom margin to define the opposite ends of the body.

BRIEF DESCRIPTION OF THE DRAWINGS

FIG. 1 is a side elevational view of a nasal packing article, in its fully hydrated and expanded state, embodying the present invention;

FIGS. 2A and 2B are sectional views of first and second slit arrangements, respectively, for the article of FIG. 1, taken along line 2—2 thereof;

FIG. 3 is a plan view of the article of FIG. 1, shown in its compressed, dry state and drawn to an enlarged scale;

FIG. 4 is a sectional view of the article as shown in FIG. 3, taken along line 4—4 thereof;

FIGS. 5 and 6 are schematic lateral and transverse sectional representations, respectively, of the human nasal cavity;

DETAILED DESCRIPTION OF THE ILLUSTRATED EMBODIMENTS

Figure 7A:
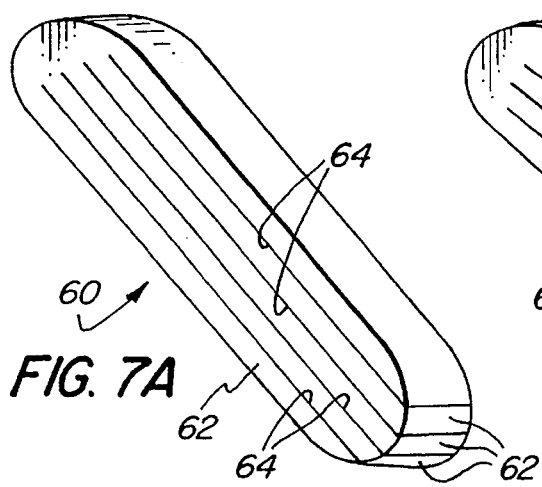
FIGS. 7A and 7B are perspective views showing an elongate, straight-sided oval form of the article, with the laminae defined by slits depicted, respectively, in close and separated relationships to one another.

Turning initially to FIGS. 1 and 2 of the appended drawings, therein illustrated is one embodiment of the nasal-packing articles of the invention, comprised of a body, generally designated by the numeral 10, formed from a porous, cellular material and shown in its expanded state. The body 10 has a top margin 14 of arched contour which merges into the bottom, rectilinear margin 16 to define opposite ends 18 thereon; it has a flat lateral surface 40 on one side, and a lateral portion on the other.

In the form shown in FIG. 2A, lower portion 42 of the face of the article on the side opposite to the surface 40 lies in a plane substantially parallel to the plane thereof, and the upper portion 46 extends at an upwardly-convergent angle. Longitudinal slits 48 extend inwardly from the surface portion 46, and normal thereto; they terminate short of the surface 40. A second set of slits 50 traverse the slits 48 and extend entirely from the face portion 46 to the surface 40, to cooperatively form six laminae disposed face to face along the length of the article, which lamina are connected at one end by the unsevered portion 49 at the bottom of the article (line 4—4 is taken on the plane in which one of the slits 50 lies).

The slits 48,50 cooperatively form a multiplicity of independently movable finger elements 52. By virtue of the latitude of differential expansion and separation thereby afforded, the elements 52 enable a high degree of conformity of the hydrated packing to the inner surfaces of the nasal cavity 30, and hence the application of effective, gentle pressure to any ruptured vessels or arteries present thereon.

In the form shown in FIG. 2B (which does not correspond strictly to FIG. 1, as will be appreciated), two slits 12 extend downwardly into the body 10, parallel to an imaginary intermedial plane 20 and at equidistantly spaced locations through the thickness thereof; slits 50 extend transversely to the slits 12, and entirely through the body thickness. The slits 12 effectively subdivide the laminae formed by slits 50, thereby cooperatively forming elements 32, 34 and 36. The elements 32, 34 36 are of different heights and terminate substantially on a plane 28 that lies obliquely to the intermedial plane 20, thus affording an effectively upward taper to the lateral surface portion thereat.

As will be appreciated, the thickness, height, taper, and arched top margin of the body 10, 10' will cause it to conform (when expanded) generally to the nasal cavity 30, as it is depicted in FIGS. 5 and 6. It will further be appreciated however that, because the elements are free to move independently and to separate from one another, and to expand differentially and selectively into gentle contact with substantially all surfaces of the cavity 30, the desired hemostatic effect is effectively produced even by packing that is of less than optimal configuration.

As is also seen in these Figures, a hollow tube 38 extends through the lower portion of the packing body. This serves of course to facilitate breathing and to thereby promote maximum comfort for the user; such a feature is of course especially desirable when both nostrils would otherwise be blocked.

The compressed state of the body 10 is illustrated in FIGS. 3 and 4. It can be seen that the tube 38 protrudes from the opposite ends 18, due of course to the reduced dimensions of the body 10 in that condition.

Figure 7B:
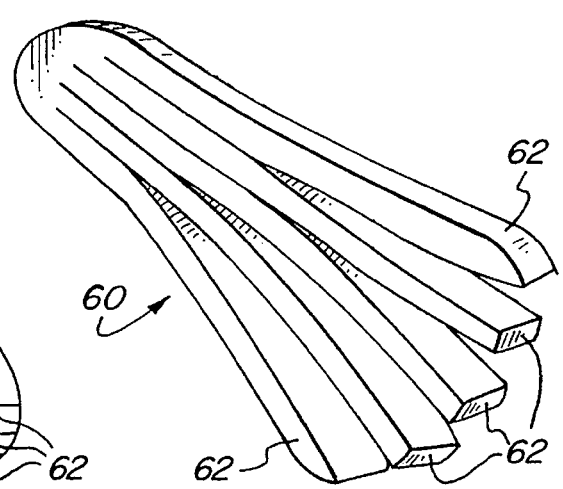
Figure 8:
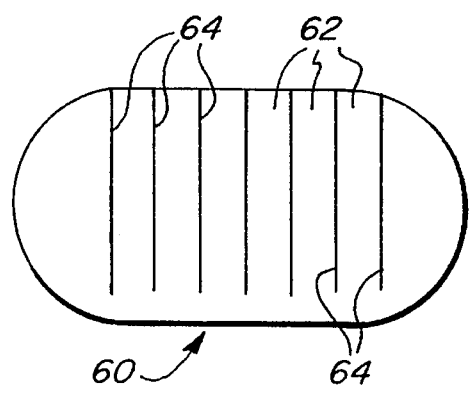
FIGS. 8 through 13 are schematic plan views of various configurations and constructions of articles embodying the present invention.
Figure 9:
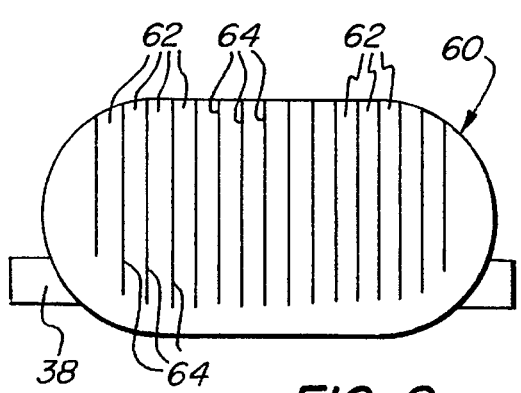
Figure 10:
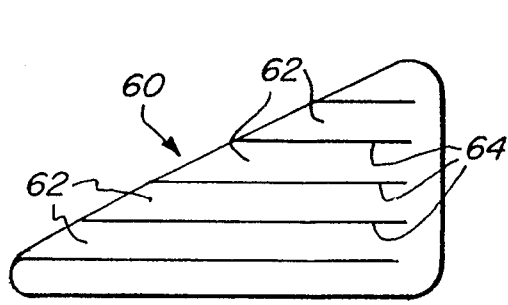
Figure 11:
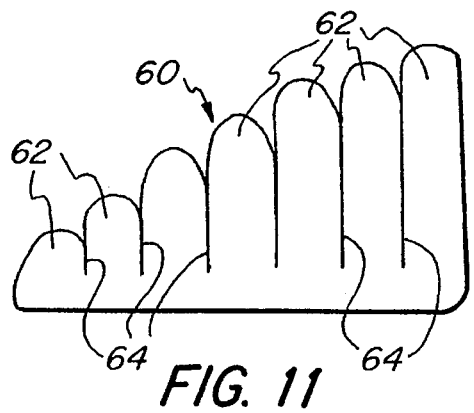
Figure 12:
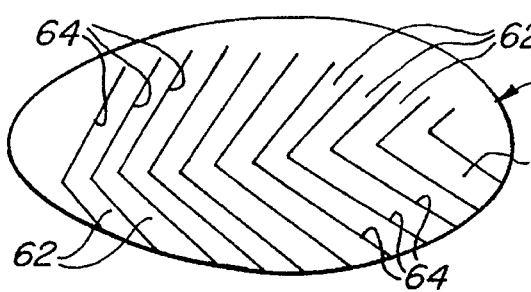
Figure 13:
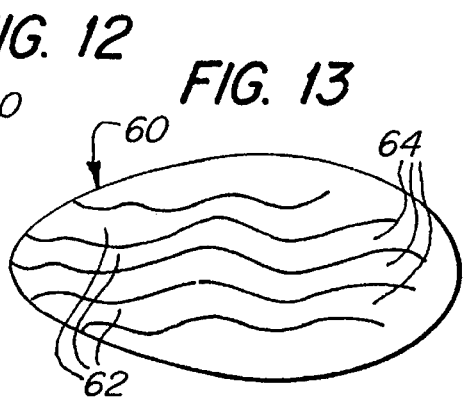
Figure 14:
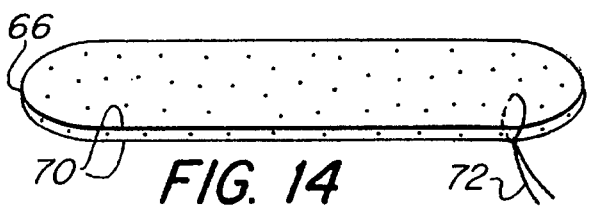
FIGS. 14 through 17 are perspective views of a preferred form of article embodying the invention, showing the article, respectively, in its fully compressed state, fully compressed and with one lamina partially removed, in its partially hydrated state, and in its fully hydrated state with the laminae separated from one another.

It will be appreciated that many variations can be made in the form and structure of the packing of the invention without departure from the scope of the appended claims. FIGS. 7A and 7B show a second form of packing article comprised of a body generally designated by the numeral 60, consisting of independently movable and separable elements 62 defined by the slits 64. The elements 62 are shown in both closed (FIG. 7A) and open, or spaced, relationship (FIG. 7B) to one another.

FIGS. 8 through 13 are plan views depicting a variety of body configurations and slit arrangements that can be employed in fabricating the instant article. In each case, the body is again generally designated by the numeral 60, the slits extend entirely through the body thickness and are designated 64, and the resultant independently movable and separable laminae are designated 62; a breathing tube 38 extends lengthwise of the article of FIG. 9. As can be seen from these Figures, the body 60 may have an oval, a straight-sided oval, and a triangular configuration, and the slits (or interfacial boundaries) may be rectilinear, curvilinear, simple, or compound; other body shapes, such as rectangular and round, and other slit arrangements and configurations, can of course be employed as well, if so desired. As is also seen in these Figures, the interconnected ends of the laminae may be disposed either at one end of the article (FIGS. 10 and 13) or along one of its side margins (FIGS. 8, 9, 11 and 12).

The packing article of FIGS. 14 through 17 represents a preferred embodiment of the invention, from structural as well as configurational standpoints. As can be seen, it is a laminar article fabricated from six identical layers 66 of thin, relatively narrow absorbent material. The layers 66 are stacked with their transverse faces 68 in direct contact and their lateral faces 70 in registry (along each side of the article), and they are compressed in the direction perpendicular (normal) to the contacting faces 68 as well as parallel to the planes thereof (widthwise, not lengthwise). The resultant laminae are bonded to one another by simple mechanical interengagement at the interfaces; i.e., they are compressed in the dry state, and no adhesive material is employed. As a typical example, an article of this kind will consist of layers 2 mm thick, 20 mm wide, and 80 mm long (all as measured with the material in its fully hydrated state). As in other embodiments, however, a wide range of dimensions, configurations and combinations may be employed. Packing in which the width dimension of a lamina is substantially greater than its thickness dimension, and its length dimension is substantially greater than its width dimension, will be preferred in many instances.

A length of string 72 extends through all six layers of the article depicted in FIGS. 14 through 17, to more securely connect the laminae at one end. Despite the previously mentioned advantages of using string, it will be appreciated that other forms of connecting means, such as those referred to hereinabove, can be substituted if preferred.

Figure 15:
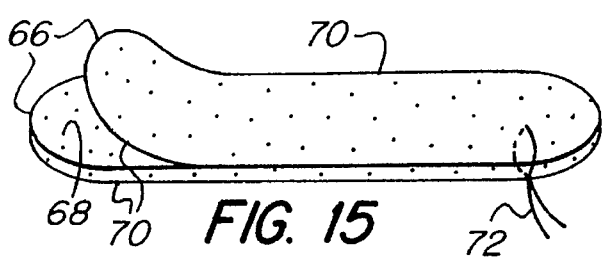
Figure 16:
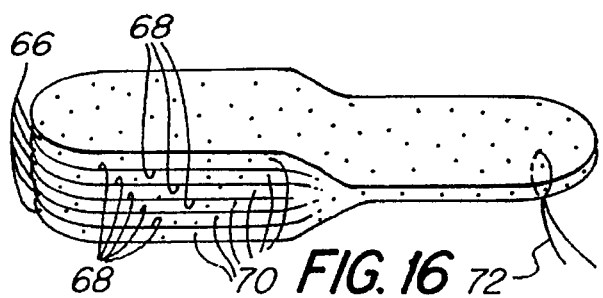
Figure 17:
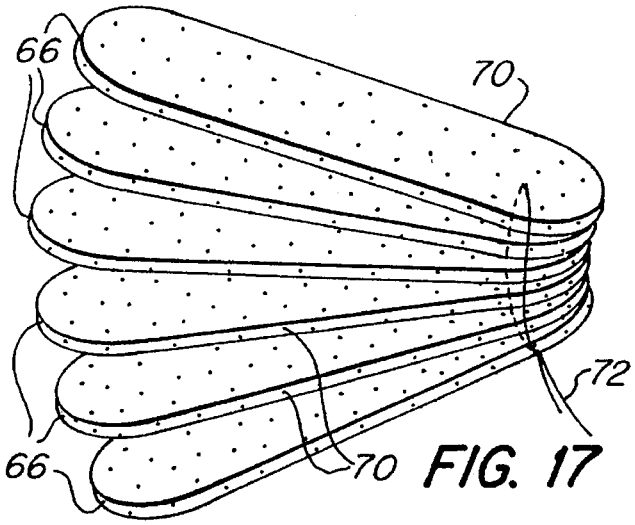
Figure 18:
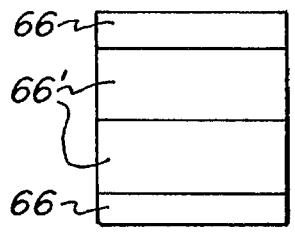
FIGS. 18 and 19 are end views of articles embodying the invention, in which the constituent laminae are of different thicknesses.
Figure 19:
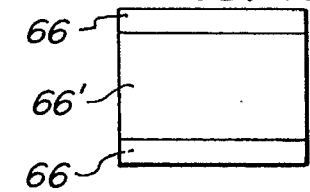
Figure 20:
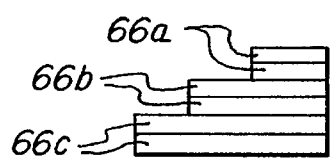
FIG. 20 is an end view of an article embodying the invention, comprised of laminae of three different widths.

FIG. 15 depicts one of the laminae 66 being peeled away from the others; a sharp can be inserted between adjacent laminae to initiate delamination, if necessary. Removal of one or more laminae (or portions thereof) constitutes a convenient way to decrease the overall thickness of the packing, as may best suit any given application. FIG. 16 shows the laminae of the article in a partially hydrated condition, and FIG. 17 shows them fully hydrated and fully separated from one another (except to the extent of being tied together by the string 72). Packing articles similar to that of FIGS. 14 through 17, but consisting of combinations of relatively thin laminae 66 and relatively thick laminae 66', are depicted in FIGS. 18 and 19, and a similar article made of different width lamina 66a, 66b and 66c are shown in FIG. 20.

Figure 21:
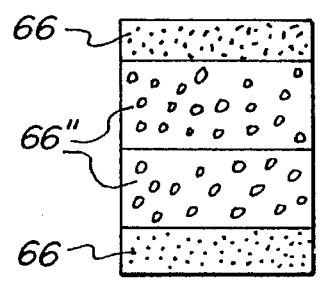
FIG. 21 is an end view of an article of the invention in which different materials are employed for the laminae, which laminae are also of different thicknesses.

FIG. 21 illustrates another laminated article embodying the invention, in which the external layers 66 are not only relatively thin, as compared to the internal layers 66", but are also made of a material having a relatively small average pore size. The advantages of such construction include a lower susceptibility of the smaller pore-size material to tissue ingrowth, coupled with the high liquid-holding capacity of the larger pore-size internal laminae 66". Variations of composition, within a single article, are also within the scope of the instant invention.

It will be appreciated that virtually any material (of suitable biological properties) that can be maintained in a compressed state, and that will expansively respond to contact by a liquid (e.g., blood, mucous, saline solution) to provide a relatively soft and absorbent body, can be used for fabrication of the packing article. Polyvinyl alcohol(PVA)/ formaldehyde reaction products, cellulose derivatives, polyurethane, and like materials known or suitable for use as surgical sponges, will normally be employed. The PVA/ formaldehyde sponge material will however often be especially preferred, due to its ability to compress from the dry state to an integrated, laminar article of dimensionally stable size and shape.

As used herein, reference to expansion in response to liquid contact implies at least a 10 percent increase from the dry state, but in many instances the increase will of course be substantially greater. It should also be appreciated that references herein to "nasal" cavities and "nasal" packing are to be broadly construed to include, for example, sinus cavities, ear canals and packing therefor.

While the body of the expanded article will advantageously be of sufficient volume to substantially fill the nasal cavity, its construction may be such as to not only allow the individual laminae to seek-out and occupy recesses, but also to be readily displaced from tight areas so as to distribute the material, and consequently the forces applied, to optimal effect. Depending upon the overall construction of the article, these functions may be achieved most effectively when the laminae are subdivided into separate fingers, as previously described. Although a single article can be dimensioned to comfortably fit most individuals, different sizes may of course be provided if so desired. Normally, the packing will have an expanded thickness, if not attenuated, of at least about 10 mm.

Techniques for manufacturing compressed articles of this kind are well known to those skilled in the art, and need not be described in detail. Briefly, the body will simply be formed, dried and compressed. As can be seen from the drawings and the corresponding text, the articles that embody the present invention are all devoid of any container of which they are comprised. Although any slits required may be produced during molding, subsequent cutting will normally be the preferred technique.

As used herein, reference to a "plurality" of laminae is intended to include articles constituted of as few as two layers, albeit that, as a practical matter, four or more laminae will generally be preferred. One reason for that preference concerns to ability to delaminate and remove one or more layers from the others, while still retaining elements that can separate and seek optimal positions within the nasal cavity. It might be mentioned moreover that an advantageous manner of use might involve division of the article into two sections, one for emplacement in the nasal passage above a turbinate, and the other for emplacement therebelow.

Thus, it can be seen that the present invention provides a novel nasal packing article that is expansible from the dry state, and that is capable of effectively applying gentle pressure to substantially all parts of the nasal cavity, including relatively inaccessible openings and recesses. The article avoids undue pressure and overpacking, it is readily inserted and removed and comfortably worn, it is of simple and inexpensive manufacture, and it functions without need for any supplemental packing.

Having thus described the invention, what is claimed is:

1. A laminar nasal packing article fabricated from a porous, absorbent, cellular material that is compressible to a dimensionally stable form, when dry, and is expansible from its dry, compressed state when wetted and is resiliently deformable in its wet, expanded state, said article comprising a plurality of laminae, each lamina having opposite ends, opposed transverse faces and opposed lateral faces, and each lamina having a length dimension, taken between said opposite ends, and a thickness dimension and a width dimension taken, respectively, between said opposed transverse faces and said opposed lateral faces, said laminae being disposed with said transverse faces of adjacent lamina in mutual, direct, full-surface contact and being compressed together in the dry state and in the direction perpendicular to said contacting transverse faces to thereby bond and unite said laminae in a stable, dry, compressed state of mechanical interengagement throughout the areas of said mutual contact, said dry laminae being devoid of any container comprising said article and being manually disengagable inwardly from one of said ends and along at least a major portion of the length of said article to enable at least partial delamination and removal of said laminae from one another, and said lamina being free to move independently and to separate from one another along said major portion in hydrated condition for effectively applying gentle pressure to substantially all parts of the nasal cavity in which said article is inserted.

2. The article of claim 1 wherein each of said laminae is of uniform thickness.

3. The article of claim 2 wherein at least one of said laminae is substantially thinner than at least one other of said laminae.

4. The article of claim 3 comprising at least two of said substantially thinner laminae, said two substantially thinner laminae being exteriorly disposed on said article.

5. The article of claim 1 wherein all of said faces are substantially planar.

6. The article of claim 1 wherein at least one of said laminae is fabricated from a first material that is substantially different from a second material, at least one other of said laminae being fabricated from said second material.

7. The article of claim 6 wherein the pores of said first material are of substantially smaller average size than the pores of said second material.

8. The article of claim 7 comprising two exterior laminae fabricated from said first material.

9. The article of claim 1 comprising at least five of said laminae, said article having an overall thickness, in its fully expanded and unattenuated form, of at least about 10 mm.

10. The article of claim 2 wherein all of said laminae are substantially identical.

11. The article of claim 1 wherein said article is uncompressed in the direction of its length.

12. The article of claim 1 additionally including connecting means serving to more permanently secure said laminae together, to maintain said full-surface contact therebetween; adjacent the other of said opposite ends.

13. The article of claim 12 wherein said connecting means comprises means selected from the class consisting of an adhesive bond, a fusion bond, a substantially rigid mechanical fastener, and a string.

14. The article of claim 12 constituted by a single piece of said material severed to form said laminae, said connecting means comprising an unsevered section of said piece adjacent said other end.

15. The article of claim 1 further including a hollow tubular element oriented lengthwise of said article and extending entirely therethrough.

16. The article of claim 1 wherein at least one of said laminae is subdivided, along at least one plane extending lengthwise of said article and perpendicular to said contacting faces, into a plurality of substantially independent fingers.

17. The article of claim 1 wherein said thickness dimension is substantially less than said width dimension.

18. The article of claim 1 wherein said length dimension is substantially greater than each of said thickness and said width dimensions.

19. A laminar nasal packing article fabricated from a porous, absorbent, cellular material that is compressible to a dimensionally stable form, when dry, and is expansible from its dry, compressed state when wetted and is resiliently deformable in its wet, expanded state, said article comprising a plurality of laminae, each lamina having opposite ends, opposed transverse faces and opposed lateral faces, and each lamina having a length dimension, taken between said opposite ends, and a thickness dimension and a width dimension taken, respectively, between said opposed transverse faces and said opposed lateral faces, said laminae being disposed with said transverse faces of adjacent lamina in mutual, direct, full-surface contact and being compressed together in the dry state and in the direction perpendicular to said contacting transverse faces to thereby bond and unite said laminae in a stable, dry, compressed state of mechanical interengagement throughout the areas of said mutual contact, said dry laminae being devoid of any container comprising said article and being manually disengagable inwardly from one of said ends and along at least a major portion of the length of said article to enable at least partial delamination and removal of said laminae from one another, and said lamina being free to move independently and to separate from one another along said major portion in hydrated condition for effectively applying gentle pressure to substantially all parts of the nasal cavity in which said article is inserted, said article further including connecting means serving to more permanently secure said laminae together, to maintain said full surface contact therebetween, adjacent the other of said opposite ends.

20. The article of claim 19 wherein said connecting means comprises means selected from the class consisting of an adhesive bond, a fusion bond, a substantially rigid mechanical fastener, and a string.

21. The article of claim 19 constituted by a single piece of said material severed to form said laminae, said connecting means comprising an unsevered section of said piece adjacent said other end.

22. The article of claim 19 comprising at least five of said laminae, said article having an overall thickness, in its fully expanded and unattenuated form, of at least about 10 mm.

* * * * *